United States Patent
Zhao et al.

(10) Patent No.: US 9,031,192 B2
(45) Date of Patent: May 12, 2015

(54) RAY EMISSION DEVICE AND IMAGING SYSTEM HAVING THE SAME

(71) Applicants: Nuctech Company Limited, Beijing (CN); Tsinghua University, Beijing (CN)

(72) Inventors: Ziran Zhao, Beijing (CN); Wanlong Wu, Beijing (CN); Yingkang Jin, Beijing (CN); Le Tang, Beijing (CN); Guangwei Ding, Beijing (CN); Chenguang Zhu, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/060,270

(22) Filed: Oct. 22, 2013

(65) Prior Publication Data

US 2014/0177802 A1    Jun. 26, 2014

(30) Foreign Application Priority Data

Oct. 24, 2012   (CN) .......................... 2012 1 0409265

(51) Int. Cl.
| | |
|---|---|
| *H05G 1/70* | (2006.01) |
| *G21K 1/04* | (2006.01) |
| *G01N 23/20* | (2006.01) |

(52) U.S. Cl.
CPC *G21K 1/04* (2013.01); *G21K 1/043* (2013.01); *G01N 23/20* (2013.01)

(58) Field of Classification Search
CPC .......................... H01J 35/065; H01J 2235/068
USPC ............................................ 378/57, 145, 149
See application file for complete search history.

(56) References Cited

U.S. PATENT DOCUMENTS

| | | | | |
|---|---|---|---|---|
| 1,730,976 | A * | 10/1929 | Jenkins | 348/200 |
| 1,963,255 | A * | 6/1934 | Zimber | 348/200 |
| 2010/0008465 | A1 * | 1/2010 | Matsuura et al. | 378/62 |
| 2012/0106714 | A1 * | 5/2012 | Grodzins et al. | 378/146 |

OTHER PUBLICATIONS

Communication including extended European Search Report for European Patent Application No. 13189826.4-1556/2725584, dated Apr. 3, 2014, 7 pages.

* cited by examiner

*Primary Examiner* — Hoon Song
(74) *Attorney, Agent, or Firm* — Westman, Champlin & Koehler, P.A.

(57) ABSTRACT

A ray emission device and an imaging system with the ray emission device are disclosed. The ray emission device comprises: a cylinder; a ray source disposed in the cylinder for emitting a ray; and a collimator disposed in the cylinder. The collimator enables the ray emitted by the ray source to form sectorial ray beams at a plurality of positions in an axial direction of the cylinder. The cylinder has a pencil beam forming part arranged over an axial length of the cylinder corresponding to the plurality of positions. The sectorial ray beams form pencil beams through the pencil beam forming part when the cylinder rotates around a rotation axis.

12 Claims, 4 Drawing Sheets

RAY EMISSION DEVICE AND IMAGING SYSTEM HAVING THE SAME

CROSS REFERENCE TO RELATED APPLICATION

This application claims priority to Chinese Patent Application No. 20121009265.8, filed Oct. 24, 2012, the contents of which are hereby incorporated by reference in their entirety.

BACKGROUND OF THE INVENTION

1. Field of the Invention

The present invention relates to a ray emission device and an imaging system having the ray emission device.

2. Description of the Related Art

Scattering imaging is generally applied by scanning an object point by point with a modulated ray pencil beam while receiving the point scanning signals by a detector. Images reflecting information of the object is acquired by one-to-one correspondence between the scanning positions and the signals when processing data. The key point lies in a method by which the ray is modulated and constrained into a pencil beam and a flying spot scanning is achieved, in such application.

In a conventional flying spot scanning method, a rotary shield with one or more collimating holes is rotated in a sectorial scanning plane of the ray so that the ray is formed into a pencil beam for a flying spot by transmitting the ray through the one or more collimating holes, thereby achieving a scanning in a first dimensional direction. In order to effectively improve detection efficiency, a detector with a large area is needed to cover a solid angle of scattered rays formed when the pencil beam hits the object as far as possible. Generally, the detector is moved (translated or rotated) with the sectorial scanning plane of ray relative to the object under inspection, thereby achieving a scanning in a second dimensional direction. The relative movement may be such that the sectorial scanning plane of ray and the detector move while the object is stationary, or the sectorial scanning plane of ray and the detector are stationary while the object moves. A set of motor drive device is needed to rotate the rotary shield when carrying out a scanning in the first dimensional direction, while another set of motor drive device is required to move the ray generating device, the rotary shield and the detector together relative to the object when performing a scanning in the second dimensional direction.

As described above, two sets of mechanical drive devices are generally used to achieve a two-dimensional scanning in the prior art flying spot scanning method, and their real-time movement positions (or angles) are interrelated, and need accurate control. The two sets of mechanical drive devices have complicated mechanical structures. If the sectorial scanning plane of ray is rotated, then there is a further problem that the moment of inertia of the rotary shield is to be overcome.

Continuous movement of the scanning in the second dimensional direction will cause an actual scanning line in the first dimensional direction not to be parallel to a movement direction in the first dimensional direction with an angle of inclination between the actual scanning line and the movement direction, thereby finally causing geometry deformation of the scan images, and deteriorating the images. The more a speed of the scanning movement in the second dimensional direction is, the more the deformation is. On the other hand, the less the speed of the scanning movement in the second dimensional direction is, the longer the entire scanning time of the system is.

Therefore, there is a need for an improved flying spot scanning method which can effectively eliminate or alleviate the above dilemma.

SUMMARY OF THE INVENTION

Accordingly, an object of the present invention is to provide a ray emission device and an imaging system which can improve quality of the image.

In accordance with an aspect of the present invention, there is provided a ray emission device, comprising: a cylinder; a ray source disposed in the cylinder for emitting a ray; and a collimator disposed in the cylinder, the collimator enabling the ray emitted by the ray source to form sectorial ray beams at a plurality of positions in an axial direction of the cylinder, wherein the cylinder has a pencil beam forming part arranged over an axial length of the cylinder corresponding to the plurality of positions, and wherein the sectorial ray beams are shaped into pencil beams through the pencil beam forming part when the cylinder rotates around a rotation axis.

In accordance with another aspect of the present invention, the pencil beam forming part is a plurality of discrete holes formed through a cylinder wall of the cylinder, or a slit formed through the cylinder wall of the cylinder.

In accordance with a further aspect of the present invention, the collimator comprises a plurality of straight line-shaped gaps arranged in the axial direction of the cylinder and the ray emitted from the ray source substantially forms the sectorial ray beams through the gaps.

In accordance with a still further aspect of the present invention, the ray source comprises a plurality of focal spots arranged in the axial direction of the cylinder and corresponding to the plurality of straight line-shaped gaps.

In accordance with an aspect of the present invention, the collimator has a plate shape and abuts against the ray source.

In accordance with an aspect of the present invention, when the cylinder is rotated, the pencil beams are formed in sequence in the axial direction of the cylinder through the pencil beam forming part.

In accordance with an aspect of the present invention, the formed sectorial ray beams are substantially aligned in the axial direction of the cylinder.

In accordance with an aspect of the present invention, the plurality of focal spots are located on the rotation axis of the cylinder.

In accordance with an aspect of the present invention, the cylinder is a hollow circular cylinder.

In accordance with an aspect of the present invention, the sectorial ray beams are substantially perpendicular to the rotation axis of the cylinder.

In accordance with an aspect of the present invention, the plurality of focal spots are independently controllable.

In accordance with an aspect of the present invention, the formed pencil beams are configured to perform a two-dimensional scan of an object.

In accordance with an aspect of the present invention, the collimator is made of a material which can shield the ray.

In accordance with an aspect of the present invention, the cylinder is made of a material which can shield the ray.

In accordance with an aspect of the present invention, there is provided an imaging system, comprising: the ray emission device as above; and a detector for receiving a scattered ray scattered from an object under inspection when a ray emitted by the ray emission device hits the object.

The ray emission device and the imaging system according to the present invention can achieve a scattering scan of the object under inspection. In the present invention, only scanning movement in the first dimensional direction is used, while the conventional scanning movement in the second dimensional direction is replaced with switching of focal spots of a multi-beam X-ray source. The switching of the focal spots can be achieved only by application of a digital control signal with a particular timing sequence. Therefore, a complicated mechanical structure of motor drive is greatly simplified and the scanning speed can be easily controlled. Since there is no scanning movement in the second dimensional direction, and there is only rotation of the rotary shield itself in one dimension, the problem that the moment of inertia of the rotary shield is to be overcome does not exist. Therefore, the present invention ensures that an actual scanning line in the first dimensional direction is always consistent with a movement direction in the first dimensional direction and geometry deformation will not occur in the scan images in principle.

DETAILED DESCRIPTION OF THE EMBODIMENTS

A further description of the invention will be made as below with reference to embodiments of the present invention taken in conjunction with the accompanying drawings.

Figure 4A:
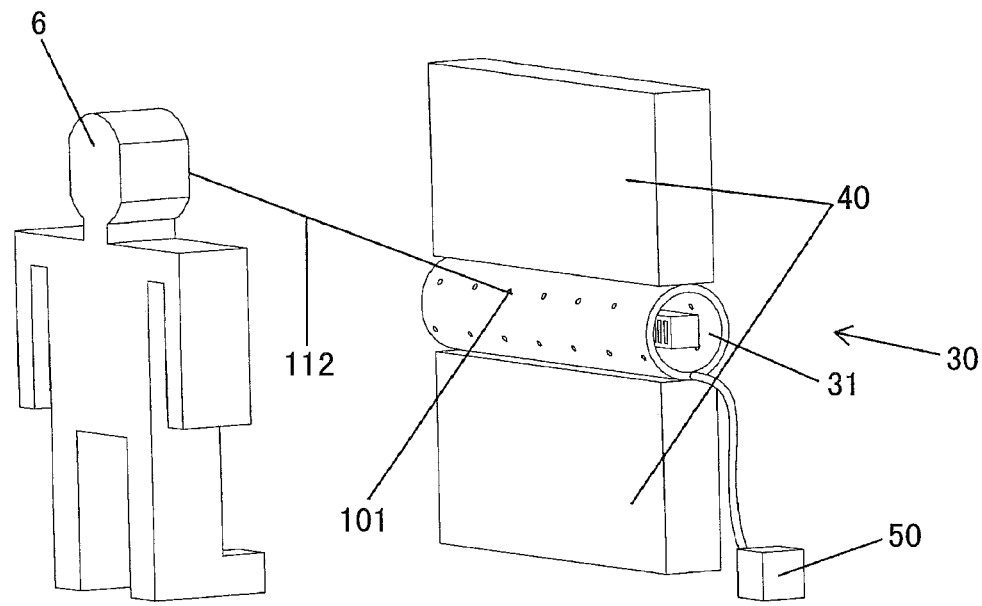
FIGS. 4a and 4b are schematic views of an imaging system according to an embodiment of the present invention.
Figure 4B:
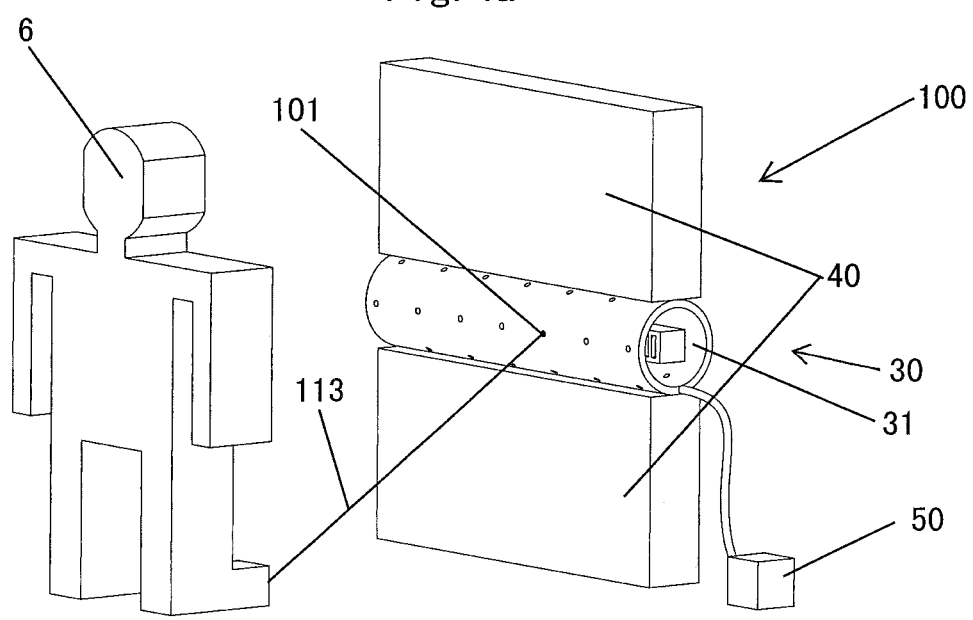

As illustrated in FIGS. 4a and 4b, an imaging system 100 according to the present invention comprises: a ray emission device 30; a scatter detector 40 for receiving a scattered ray scattered from an object 6 under inspection when a ray emitted by the ray emission device 30 hits the object, and a control part 50.

Figure 1:
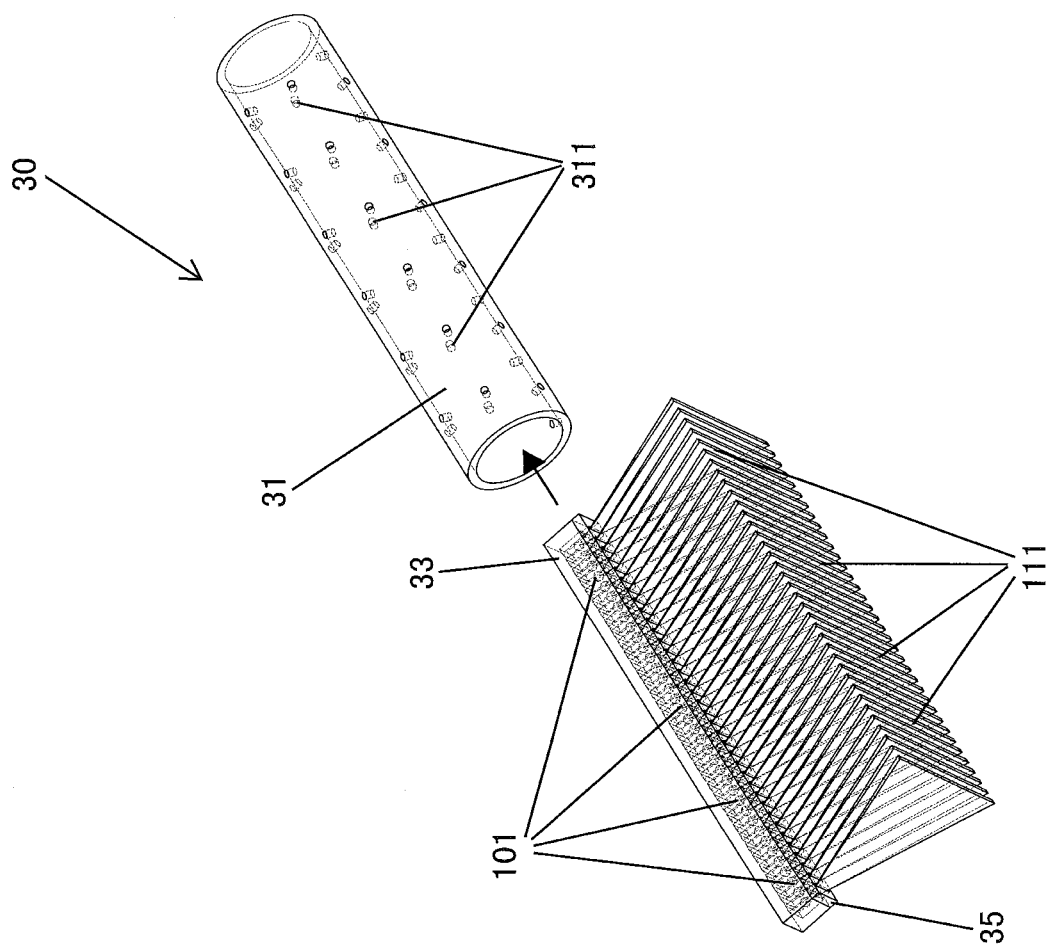
FIG. 1 is a schematic view of a ray emission device according to an embodiment of the present invention.

Referring to FIG. 1, the ray emission device 30 comprises: a cylinder 31; a ray source 33 disposed in the cylinder 31 for emitting a ray; and a collimator 35 disposed in the cylinder 31. The collimator 35 enables the ray emitted by the ray source 33 to form sectorial ray beams 111 at a plurality of positions in an axial direction of the cylinder 31. The cylinder 31 has a pencil beam forming part 311 arranged over an axial length of the cylinder 31 corresponding to the plurality of positions. The sectorial ray beams 111 are shaped into pencil beams through the pencil beam forming part 311 when the cylinder 31 rotates around a rotation axis.

Figure 2A:
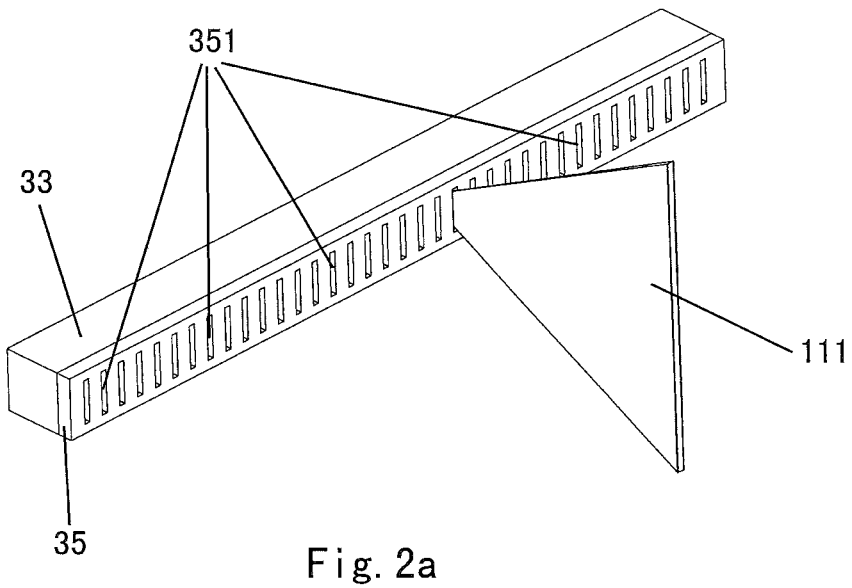
FIG. 2a is a schematic view of a ray source and a collimator according to an embodiment of the present invention in which only one of focal spots emits rays.
Figure 2B:
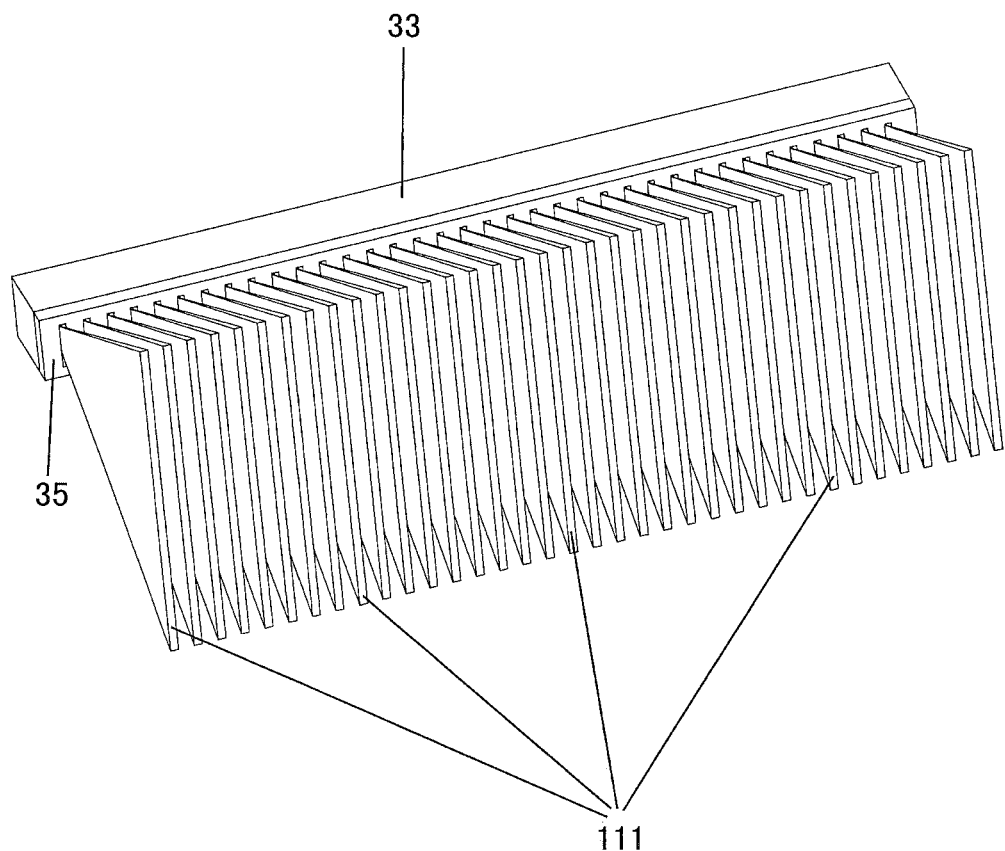
FIG. 2b is a schematic view of the ray source and the collimator according to the embodiment of the present invention in which all of the focal spots emit rays.

As illustrated in FIGS. 1, 2a and 2b, the ray source 33 may be any appropriate existing multi-beam ray source. For example, the ray source 33 may comprise a plurality of focal spots 101 arranged in the axial direction of the cylinder 31. The plurality of focal spots 101 are located on the rotation axis of the cylinder 31. The rotation axis may be a central axis of the cylinder 31. The plurality of focal spots 101 may be independently controllable. In addition, the ray source 33 may be an X-ray source. Each focal spot 101 can emit rays independently, and can be controlled by an external control signal to emit rays separately in a particular sequence. FIGS. 2a and 2b illustrate situations where the focal spots of the ray source 33 emit rays separately and simultaneously, respectively.

As illustrated in FIGS. 1, 2a and 2b, the collimator 35 comprises a plurality of straight line-shaped gaps 351 arranged in the axial direction of the cylinder 31 and the ray emitted from the ray source 33 substantially forms the sectorial ray beams 111 through the gaps 351. The plurality of focal spots 101 may correspond to the plurality of straight line-shaped gaps 351. The collimator 35 has a plate shape and abuts against the ray source 33.

The collimator 35 may be a stationary shield plate. The stationary shield plate is stationary relative to the ray source 33. The collimator 35 is made of a material, such as lead, tungsten, copper, steel, and lead tetraoxide, and preferably lead, which can shield the X-ray. The plurality of straight line-shaped gaps 351 are formed in the stationary shield plate. The ray emitted by the X-ray source 33 becomes the sectorial ray beams 111 after being collimated by the straight line-shaped gaps 351 in the stationary shield plate.

Figure 3:
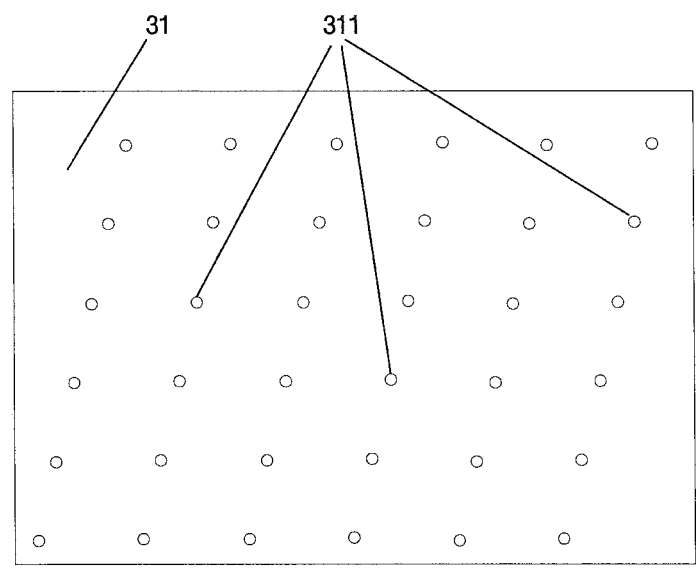
FIG. 3 is a deploying drawing of a cylinder according to an embodiment of the present invention.

As illustrated in FIGS. 1 and 3, the cylinder may be a hollow circular cylinder or a hollow cylinder having another shape. The pencil beam forming part 311 is a plurality of discrete holes 311 formed through a cylinder wall of the cylinder 31, or a slit formed through the cylinder wall of the cylinder 31. The slit may be a linear slot formed by connecting these through holes 311 and through which the ray can pass. The pencil beam forming part may have a shape of a circle, a rectangle, a rhombus, an ellipse or the like, and preferably a circle.

As illustrated in FIGS. 1, 3, 4a, and 4b, when the cylinder 31 rotates, the sectorial ray beams 111 can form the pencil beams through the pencil beam forming part 311 in sequence or in other orders in the axial direction of the cylinder 31, respectively. In other words, the pencil beams corresponding to the plurality of sectorial ray beams 111 can be formed one by one or at intervals in the axial direction of the cylinder 31, or they can be formed in other manners. The formed pencil beams are configured to perform a two-dimensional scan of an object. The formed sectorial ray beams 111 may be substantially aligned in the axial direction of the cylinder 31. The sectorial ray beams 111 may be substantially perpendicular to the rotation axis of the cylinder 31.

The cylinder 31 may be a rotary shield and is made of a material which can shield the X-ray. The cylinder 31 may be formed of a single material such as lead, tungsten, copper, steel, and lead tetraoxide, or combination of the materials, and preferably a single material selected from the above group. A typical manner in which the cylinder is formed of combination of materials is as follows. The hollow cylinder consists of three cylinders fitted together. The outmost cylinder and the innermost cylinder are made of material, such as aluminum or steel, which has certain stiffness and hardness for fixation, while the intermediate cylinder is made of typical ray shielding material, such as lead, lead-antimony alloy, and tungsten, for shielding ray.

As illustrated in FIGS. 4a, and 4b, the focal spots 101 of the ray source 33 may be configured such that one of the focal spots 101 of the ray source 33 can be aligned with only one of the holes 311 and emit a pencil beam without obstruction. As the cylinder 31 rotates, the control part 50 controls the focal spot 101 to emit ray, and the pencil beam 112 emitted from the focal spot 101 moves along a straight line on the object 6 to complete a row of scan of the object. As, the cylinder 31 has rotated is by an angle, another one of the focal spots 101 of the ray source 33 can be aligned with another one of the holes 311. The control part 5 controls the other focal spot 101 to emit ray, and the pencil beam 113 emitted from the other focal spot moves along another straight line on the object to complete another row of scan of the object. And so on, as the cylinder 31 rotates at a uniform speed, the control part 5 controls the respective focal spots of the ray source 33 to emit the ray in sequence based on rotational position information of the cylinder 31 so as to complete the entire scan of the object 6 row by row. It needs only one-dimensional movement, i.e., the rotation of the cylinder 31, for the device to complete the scan.

The detector 40 can acquire the rays scattered from the object 6 when the pencil beams hit the object 6, convert the scattered rays into digital data and transmit the same to a computer or the control part 50 for processing.

The control part 50 can control the cylinder 31 to rotate, and control the respective emission focal spots 101 of the ray source 33 to emit the X-ray based on a rotational position of the cylinder 31.

After the ray emitted from any of the focal spots of the ray source 33 is collimated by the collimator 35, only a portion of the ray that can pass through the hole 311 of the cylinder 31 can become the emitted pencil beam finally used for scan, while the rest is all shielded. The control part 5 drives the cylinder 31 to rotate so that the scanning movement in the first dimensional direction can be achieved. In addition, the control part 5 acquires angular position information of the cylinder 31 and controls the respective focal spots of the ray source 33 to emit rays based on a predetermined timing sequence so as to achieve the scanning movement in the second dimensional direction. The detector 40 acquires the pencil beam of the ray acting on the object 6 and generates digital data. The scatter image is obtained by correspondence between the digital data and the positions of the acting points of the pencil beam of the ray.

As described above, the present invention provides a ray emission device and an imaging system having the same. The ray emission device and the imaging system according to the present invention can achieve a scattering scan of the object under inspection. In the present invention, only scanning movement in the first dimensional direction is used, while the conventional scanning movement in the second dimensional direction is replaced with switching of focal spots of a multi-beam X-ray source. The switching of the focal spots can be achieved only by application of a digital control signal with a particular timing sequence. Therefore, a complicated mechanical structure of motor drive is greatly simplified and the scanning speed can be easily controlled. Since there is no scanning movement in the second dimensional direction, and there is only rotation of the rotary shield itself in one dimension, the problem that the moment of inertia of the rotary shield is to be overcome does not exist. Therefore, the present invention ensures that an actual scanning line in the first dimensional direction is always consistent with a movement direction in the first dimensional direction and geometry deformation will not occur in the scan images in principle.

What is claimed is:
1. An X-ray emission device, comprising:
a cylinder;
a multi-beam X-ray source disposed in the cylinder, the multi-beam X-ray source comprising a plurality of focal spots which are arranged at a plurality of positions in an axial direction of the cylinder and each of which is configured to emit an X-ray; and
a collimator disposed in the cylinder, the collimator enabling the X-rays emitted by the plurality of focal spots to form sectorial ray beams at the plurality of positions in the axial direction of the cylinder,
wherein the cylinder has a pencil beam forming part arranged over an axial length of the cylinder corresponding to the plurality of positions, and wherein the sectorial ray beams form pencil beams through the pencil beam forming part when the cylinder rotates around a rotation axis.

2. The X-ray emission device of claim 1, wherein the pencil beam forming part is a plurality of discrete holes formed through a cylinder wall of the cylinder.

3. The X-ray emission device of claim 1, wherein the pencil beam forming part is a slit formed through a cylinder wall of the cylinder.

4. The X-ray emission device of claim 1, wherein the collimator comprises a plurality of straight line-shaped gaps arranged in the axial direction of the cylinder and the X-rays emitted from the plurality of focal spots substantially forms the sectorial ray beams through the gaps.

5. The X-ray emission device of claim 4, wherein
the plurality of focal spots correspond to the plurality of straight line-shaped gaps.

6. The X-ray emission device of claim 1, wherein
when the cylinder is rotated, the pencil beams are formed in sequence in the axial direction of the cylinder through the pencil beam forming part.

7. The X-ray emission device of claim 5, wherein
the plurality of focal spots are located on the rotation axis of the cylinder.

8. The X-ray emission device of claim 1, wherein
the cylinder is a hollow circular cylinder.

9. The X-ray emission device of claim 1, wherein
the sectorial ray beams are substantially perpendicular to the rotation axis of the cylinder.

10. The X-ray emission device of claim 1, wherein
the collimator is made of a material which can shield X-rays.

11. The X-ray emission device of claim 1, wherein
the cylinder is made of a material which can shield X-rays.

12. An imaging system, comprising:
the X-ray emission device of claim 1; and
a detector for receiving a scattered X-ray scattered from an object under inspection when an X-ray emitted by the X-ray emission device hits the object.

* * * * *